United States Patent [19]

Cuberes-Altisent et al.

[11] Patent Number: 5,641,781
[45] Date of Patent: Jun. 24, 1997

[54] TOPICAL OPHTHALMIC COMPOSITION COMPRISING A 2-[4-(AZOLYLBUTYL) PIPERAZINYLMETHYL]BENZIMIDAZOLE DERIVATIVE, IN PARTICULAR FOR THE TREATMENT OF ALLERGIC CONJUNCTIVITIS

[75] Inventors: Maria Rosa Cuberes-Altisent, Sant Cugat del Valles; Jordi Frigola-Constansa, Barcelona, both of Spain

[73] Assignee: Laboratorios Del Dr. Esteve, S.A., Barcelona, Spain

[21] Appl. No.: 613,843

[22] Filed: Mar. 11, 1996

[30] Foreign Application Priority Data

Mar. 14, 1995 [FR] France ................... 95 02910

[51] Int. Cl.$^6$ ................... A61K 31/495
[52] U.S. Cl. ................... 514/253
[58] Field of Search ................... 514/253

[56] References Cited

U.S. PATENT DOCUMENTS

| | | | |
|---|---|---|---|
| 5,182,280 | 1/1993 | Cuberes-Altisent et al. | 514/252 |
| 5,214,040 | 5/1993 | Cuberes-Altisent et al. | 514/218 |
| 5,441,958 | 8/1995 | Yanni et al. | 514/253 |

Primary Examiner—Raymond Henley, III
Attorney, Agent, or Firm—Dressler, Rockey, Milnamow & Katz, Ltd.

[57] ABSTRACT

The present invention relates to a topical ophthalmic composition comprising at least one compound of general formula I

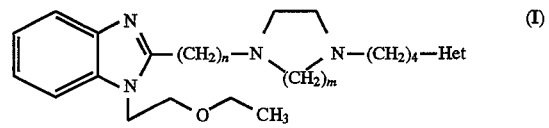

in which n may have the values 0 or 1, m may have the values 2 or 3, and Het represents a heteroaromatic radical of formula

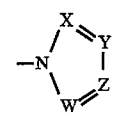

in which X, Y, Z and W, which may be the same or different, represent a nitrogen atom or a carbon atom linked to a hydrogen atom, a halogen atom, a methyl radical, an ethyl carboxylate radical, a carboxylic radical or a sulphonic radical, and the pharmaceutically acceptable salts thereof, combined with an ophthalmically acceptable vehicle, in particular for the treatment of allergic conjunctivitis.

2 Claims, No Drawings

TOPICAL OPHTHALMIC COMPOSITION COMPRISING A 2-[4-(AZOLYLBUTYL) PIPERAZINYLMETHYL]BENZIMIDAZOLE DERIVATIVE, IN PARTICULAR FOR THE TREATMENT OF ALLERGIC CONJUNCTIVITIS

The present invention relates to the use of 2-[4-azolybutyl)piperazinyl (methyl)]benzimidazole derivatives and analogues, as well as to the physiologically acceptable salts thereof, for the manufacture of ophthalmic medicinal products for topical use, which are intended for the treatment of allergic conjunctivitis and other related diseases.

The compounds to which the present invention relates have been described in the approaches in European Patents EP 468,884 and EP 507,696 as antihistamines.

We have now discovered that 2-[4-(azolylbutyl)-piperazinyl(methyl)]benzimidazole derivatives and analogues are useful for the treatment of allergic conjunctivitis and other related diseases. In particular, the compounds which for the subject of the present invention are intended for preventive or curative ophthalmic treatments for topical use in meals, including man.

The compounds recommended within the context of the present invention correspond to the general formula I

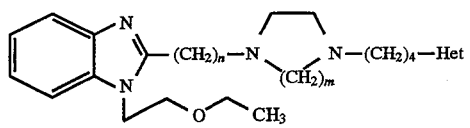

in which
n may have the values 0 or 1,
m may have the values 2 or 3,
and Het represents a heteroaromatic radical of formula

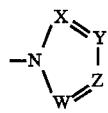

in which
X, Y, Z and W, which may be the same or different, represent a nitrogen atom or a carbon atom linked to a hydrogen atom, a halogen atom, a methyl radical, an ethyl carboxylate radical, a carboxylic radical or a sulphonic radical, and the pharmaceutically acceptable salts thereof.

The compounds identified by Examples 1 to 19 are obtained by the procedures described in European patent applications EP 468,884 and EP 507,696, and the data for their identification are given in Tables 1 and 2. The examples illustrate the properties of a few derivatives falling within the context of the present invention.

The symptoms of allergic conjunctivitis, which is relatively common, are stinging and redness of the eyes, moist, teary eyes, swollen eyelids and oedema of the conjunctiva. Conventional therapy consists mainly of the topical use of sodium cromoglycate, topical vasoconstrictors combined with antihistamines, and, in severe cases, of the use of topical corticosteroids. However, these treatments are only moderately effective. The side effects and the need for frequent administration of these therapies have driven the search for other, more satisfactory alternatives (Dechat, K. L. and Goa, K. L. "Levocabastine. A review of its pharmacological properties and therapeutic potential as a topical antihistamine in allergic rhinitis and conjunctivitis", Drugs, 1991, 41, 202–224).

We have now discovered that 2-[4-(azolylbutyl)-piperazinyl (methyl)]benzimidazole derivatives show powerful antiallergic ocular activity with an exceptionally long duration of action.

Advantageously, Het represents a pyrolyl radical (X, Y, Z and W are other than a nitrogen atom), a pyrazolyl radical (X=N, Y, Z and W are other than a nitrogen atom), an imidazolyl radical (Y=N, X, Z and W are other than a nitrogen atom) and a triazolyl radical (X=Z=N, Y and W are other than a nitrogen atom). The halogen atoms are preferably selected from chlorine and bromine.

The present invention thus relates to a topical ophthalmic composition comprising at least one compound of general formula I, as defined above, combined with an ophthalmically acceptable vehicle.

In contrast with the other oral or injectable formulations described in the prior art, the topical ophthalmic compositions correspond to specific technical characteristics associated with their application to the eyes, with the use of ophthalmically acceptable vehicles which avoid inducing various reactions that are harmful to the ophthalmic treatment such as, for example, closure of the eyelids, secretion of tears, painful reactions or alternatively redness of the conjunctiva. In particular, the excipients should be selected such that the ophthalmic composition does not trigger a secretion of tears which would instantaneously entrain the active principle. Acceptable ophthalmic excipients are well known to a person skilled in the art, who will know how to select them depending on the formulation he will select.

The ophthalmic compositions according to the invention are advantageously in the form of eye drops, ophthalmic ointments, gels or ophthalmic inserts.

The present invention also relates to the use of the compounds of general formula I above, for the preparation of a medicinal product intended for the treatment of allergic conjunctivitis and other related diseases in mammals, including man.

TABLE 1

| Ex No. | n | m | X | Y | Z | W | Sel | IR (cm$^{-1}$) film |
|---|---|---|---|---|---|---|---|---|
| 1 | 1 | 2 | N | CH | CH | CH | * | (KBr) 1693, 1618, 1470, 1362, 868 |
| 2 | 1 | 2 | N | CH | CBr | CH | — | 2937, 2808, 1465, 1117, 952, 747 |
| 3 | 0 | 2 | N | CH | CBr | CH | * | (KBr) 2975, 2881, 1706, 1619, 1475, 1356, 862, 744, 650 |
| 4 | 1 | 2 | CH | N | CH | CH | — | 2938, 2812, 1463, 1132, 749, 665 |
| 5 | 1 | 2 | N | CH | N | CH | — | 2940, 2812, 1673, 1463, 1332, 1136, 1011, 749 |
| 6 | 1 | 2 | N | CH | C—SO$_3$H | CH | — | 3600–2800, 1662, 1464, 1220, 1183, 1129, 1052, 670 |
| 7 | 1 | 2 | N | CH | C—CO$_2$H | CH | — | 3600–3200, 2931, 1706, 1462, 1119, 756 |
| 8 | 1 | 2 | N | CH | CH | CH | — | 2838, 2825, 1512, 1462, 1125, 913, 731 |
| 9 | 1 | 2 | CH | CH | CH | CH | — | 2970, 1643, 1463, 1416, 1332, 1120, 749 |
| 10 | 0 | 2 | N | CH | C—CO$_2$H | CH | — | 3360–3150, 2944, 1700, 1525, 1469, 1412, 1125, 750 |

TABLE 1-continued

| Ex No. | n | m | X | Y | Z | W | Sel | IR (cm$^{-1}$) film |
|---|---|---|---|---|---|---|---|---|
| 11 | 1 | 2 | N | CH | C—CO$_2$Et | CH | — | 1715, 1960, 1470, 1225, 1120, 1040, 750 |
| 12 | 0 | 2 | N | CH | C—CO$_2$Et | CH | — | (KBr) 1715, 1220, 1125, 760 |
| 13 | 1 | 2 | CH | N | CCl | CCl | — | 2940, 2810, 1463, 1254, 749, 666 |
| 14 | 1 | 3 | N | CH | CH | CH | — | 2938, 2869, 1464, 1119, 748, 619 |
| 15 | 1 | 3 | CH | CH | CH | CH | — | 2936, 2870, 1463, 1120, 745, 725 |
| 16 | 1 | 3 | CMe | N | CCl | CCl | — | 2937, 1464, 1408, 1246, 1120, 746 |
| 17 | 0 | 3 | N | CH | CH | CH | * | (KBr) 3000, 2890, 1619, 1579, 1470, 1358 |
| 18 | 0 | 3 | N | CH | C—CO$_2$H | CH | — | 3600–3150, 1571, 1432, 670 |
| 19 | 0 | 3 | N | CH | C—CO$_2$Et | CH | — | 1715, 1565, 1465, 1120, 1040, 750 |

*dimaleate

TABLE 2

| Example | 1H-NMR δ (CDCl$_3$) |
|---|---|
| 1 | 1.01(t, 3H); 1.57(m, 2H); 1.79(m, 2H); 2.70(m, 4H); 3.08(t, 2H); 3.20(m, 4H); 3.37(q, 2H); 3.71(t, 2H); 3.97(s, 2H); 4.14(t, 2H); 4.51(t, 2H); 6.15(s, 4H); 6.23(m, 1H); 7.26(m, 2H); 7.43(d, 1H); 7.62(m, 2H); 7.71(d, 1H) (DMSO-d$_6$) |
| 2 | 1.12(t, 3H); 1.46(m, 2H); 1.81(m, 2H); 2.45(m, 10H); 3.41(q, 2H); 3.81(m, 4H); 4.08(t, 2H); 4.50(t, 2H); 7.33(m, 5H); 7.69(m, 1H) |
| 3 | 1.13(t, 3H); 1.60(m, 2H); 1.87(m, 2H); 2.55(t, 2H); 2.76(m, 4H); 3.44(m, 6H); 3.81(t, 2H); 4.12(dt, 4H); 7.12–7.61 (m, 6H) |
| 4 | 1.12(t, 3H); 1.70(m, 4H); 2.35(m, 10H); 3.40(q, 2H); 3.75(m, 6H); 4.35(t, 2H); 6.9(s, 1H); 7.0(s, 1H); 7.18–7.45 (m, 4H); 7.7(m, 1H); |
| 5 | 1.13(t, 3H); 1.46(m, 2H); 1.90(m, 2H); 2.45(m, 10H); 3.42(q, 2H); 3.76(t, 2H); 3.88(s, 2H); 4.20(t, 2H); 4.52(t, 2H); 7.30(m, 3H); 7.71(m, 1H); 7.94(s, 1H); 8.06(s, 1H); |
| 6 | 1.0(t, 3H); 2.11(m, 4H); 3.67(m, 16H); 4.37(t, 2H); 4.65(t, 2H); 7.7(m, 6H) (DMSO-d$_6$) |
| 7 | 1.10(t, 3H); 1.58(m, 2H); 1.86(m, 2H); 2.68(m, 10H); 3.38(q, 2H); 3.73(t, 2H); 3.89(s, 2H); 4.15(t, 2H); 4.48(t, 2H); 7.27(m, 3H); 7.84(m, 3H) |
| 8 | 1.12(t, 3H); 1.50(m, 2H); 1.85(m, 2H); 2.45(m, 10H); 3.41(q, 2H); 3.75(t, 2H); 3.87(s, 2H); 4.14(t, 2H); 4.50(t, 2H); 6.22(m, 1H); 7.19–7.47(m, 6H) |
| 9 | 1.1(t, 3H); 1.70(m, 4H); 2.69(m, 10H); 3.40(q, 2H); 3.55–3.90(m, 6H); 4.46 (t, 2H); 6.12(m, 2H); 6.62(m, 2H); 7.1–7.7(m, 4H) |
| 10 | 1.14(t, 3H); 1.59(m, 2H); 1.90(m, 2H); 2.4–2.8(m, 6H); 3.3–3.6(m, 6H); 3.83 (t, 2H); 4.17(dt, 4H) |
| 11 | 1.12(t, 3H); 1.45(m, 5H); 1.90(m, 2H); 2.44(m, 10H); 3.41(q, 2H); 3.60–3.86 (m, 4H); 4.0–4.3(m, 4H); 4.50(t, 2H); 7.28(m, 3H); 7.75(m, 1H); 7.8(s, 2H) |
| 12 | 1.1(t, 3H); 1.3(t, 3H); 1.8(m, 4H); 2.15–2.7(m, 6H); 3.25(m, 6H); 3.7 (t, 2H); 3.8–4.3(m, 6H); 7.2(m, 3H); 7.5 (m, 1H); 7.8(s, 2H) |
| 13 | 1.12(t, 3H); 1.55(m, 2H); 1.80(m, 2H); 2.1–2.6(m, 10H); 3.41(q, 2H); 3.86 (m, 6H); 4.49(t, 2H); 7.29(m, 4H); 7.75 (m, 1H) |
| 14 | 1.11(t, 3H); 1.41(m, 2H); 1.79(m, 4H); 2.37–2.74(m, 10H); 3.39(q, 2H); 3.75 (t, 2H); 3.96(s, 2H); 4.12(t, 2H); 4.55 (t, 2H); 6.22(é, 1H); 7.2–7.47(m, 5H); 7.68(m, 1H) |
| 15 | 1.11(t, 3H); 1.47(m, 2H); 1.82(m, 4H); 2.48(S, 2H); 2.73(m, 8H); 3.39(q, 2H); 3.75(t, 2H); 3.87(t, 2H); 3.97(s, 2H); 4.53(t, 2H); 6.11(m, 2H); 6.63(m, 2H); 7.25(m, 3H); 7.67(m, 1H) |
| 16 | 1.11(t, 3H); 1.5–1.9(m, 6H); 2.36 (s, 3H); 2.5–2.9(m, 10H); 3.39(q, 2H); 3.7–3.9(dt, 4H); 3.99(s, 2H); 4.54 (t, 2H); 7.26(m, 3H); 7.68(m, 1H) |
| 17 | 1.13(t, 3H); 1.46(m, 2H); 1.95(m, 4H); 2.52(t, 2H); 2.79(m, 4H); 3.34–3.81 (m, 8H); 4.05–4.19(dt, 4H); 6.20(m, 1H); 7.0–7.5(m, 6H) |
| 18 | 0.93(t, 3H); 1.3–2.0(m, 6H); 2.6(m, 2H); 2.95(m, 4H); 3.17–3.62(m, 8H); 4.11 (m, 4H); 7.1(m, 3H); 7.4(m, 1H); 7.87 (s, 1H); 7.97(s, 1H) (D$_2$O) |
| 19 | 1.13(t, 3H); 1.33(t, 3H); 1.93(m, 6H); 2.6(t, 2H); 2.8(m, 4H); 3.35–3.82 (m, 8H); 4.07–4.4(m, 6H); 7.1–7.25 (m, 3H); 7.5(m, 1H); 7.85(s, 2H) |

Study of the Topical Treatment of Allergic Conjunctivitis

The ocular antihistaminic topical effect of the products which form the subject of the present invention was evaluated by means of a model of microvascular permeability in guinea pig conjunctiva, induced by histamine. In this animal model of ocular antiallergic activity, the power, the fifty percent effective dose and the duration of action are measured.

Microvascular Permeability in Guinea Pig Conjunctiva Induced by Histamine (Extravasation of Evans Blue Dye)

Male VAF Dunkin/Hartley guinea pigs (6 per group) are injected intravenously, into the marginal vein of the ear, with 1.0 ml of Evans blue (1.0 mg/ml). Approximately 15 minutes after injection of the dye, 20 μl of the appropriate concentration of the compound of Example 1 or of the vehicle are applied topically to an eye of each of the animals. 2 minutes, 30 minutes and 6 hours after the topical application, the guinea pigs are anaesthetized and histamine (300 ng/10 μl) is administered to them subconjunctivally. Thirty minutes later the animals are sacrificed by inhalation of $CO_2$ and the area of extravasation of the Evans blue is measured. The area of the blue dye is multiplied by the intensity of the colour, graded from 1 to 6, in order to produce a value of permeability for each animal (Yauni et al., *Int. Arch. Allergy Immunol.*, 1993, 101, 102–106). The values obtained by the groups treated are then compared with those obtained with the group treated with the vehicle using Dunnett's "t" test (Dunnett C. W. "A multiple comparison procedure for comparing treatments with a control", *J. Am Stat. Assoc* 1955, 50, 1096–1121)

The compound of Example 1 inhibits, significantly and in a dose-dependent manner, the vascular permeability induced by histamine in the guinea pig conjunctiva after an ocular topical administration. This inhibition is observed in a range of concentrations from 0.1% to 0.0001% weight/volume. The data obtained are presented in Table 3. The $ED_{50}$, defined as the concentration of compound which produces a 50% inhibition of the vascular permeability in comparison with the values of the control group, was 0.0024 w/v at 2 minutes, 0.00035 w/v at 30 minutes and 0.00043 w/v at 8 hours. These results (Table 3) demonstrate a powerful antihistaminic activity accompanied by an exceptionally long duration of action.

TABLE 3

| Compound concentration | Degree of permeability ($\bar{X} \pm SD$) | | | % change | | |
|---|---|---|---|---|---|---|
| % (w/v) | 2' | 30' | 6 h | 2' | 30' | 6 h |
| Vehicle | 290 ± 50 | 278 ± 17 | 278 ± 50 | — | — | — |
| Example 1    0.1 | 73 ± 10* | 0 ± 0* | 0 ± 0* | −75 | −100 | −100 |
| 0.01 | 99 ± 40* | 42 ± 15* | 25 ± 10* | −66 | −85 | −91 |
| 0.001 | 171 ± 40* | 95 ± 68* | 94 ± 20* | −41 | −66 | −66 |
| 0.0001 | — | 154 ± 10* | 179 ± 30* | — | −45 | −36 |
| 0.00001 | — | 262 ± 40 | 269 ± 28 | — | −6 | −3 |
| $ED_{50}$ (% w/v) | | | | 0.0024 | 0.00035 | 0.00043 |

*p < 0.01, Dunnett's t test

In human therapy, the dose administered obviously depends on the seriousness of the complaint to be treated. The derivatives of the invention will, for example, be administered in the form of a solution, a dispersion or a gel.

Specific pharmaceutical formulations for one of the derivatives which forms the subject of the present invention will be given below, by way of example. Obviously, the same types of compositions may be prepared by replacing the compound of Example 1 by the compounds of Examples 2 to 19, and the excipients by their equivalents.

| Composition | Formula I | Formula II | Formula III |
|---|---|---|---|
| Example 1 | 0.200 g | 0.500 g | 1.000 g |
| Benzalkonium chloride | 0.015 g | 0.015 g | 0.015 g |
| Edetate disodium | 0.015 g | 0.015 g | 0.015 g |
| Sodium chloride | 0.560 g | 0.480 g | 0.360 g |
| Monosodium phosphate dihydrate | 0.105 g | 0.105 g | 0.105 g |
| Disodium phosphate dodecahydrate | 0.955 g | 0.955 g | 0.955 g |
| Hydroxymethylcellulose | 0.300 g | 0.300 g | 0.300 g |
| Purified sterile water qs | 100.000 ml | 100.000 ml | 100.000 ml |

We claim:

1. Topical ophthalmic composition in the form of an ophthalmic ointment, of a gel or of an ophthalmic insert that comprises at least one compound of general formula I

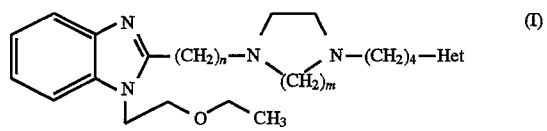

in which n may have the values 0 or 1, m may have the values 2 or 3, and Het represents a heteroaromatic radical of formula

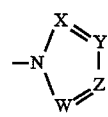

in which

X, Y, Z and W, which may be the same or different, represent a nitrogen atom or a carbon atom linked to a hydrogen atom, a halogen atom, a methyl radical, an ethyl carboxylate radical, a carboxylic radical or a sulphonic radical, and the pharmaceutically acceptable salts thereof, combined with an ophthalmically acceptable vehicle.

2. A method of treating a patient suffering from allergic conjunctivitis that comprises administering an effective amount to the eye(s) of a patient in need of such treatment a compound of general Formula I

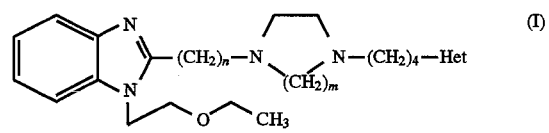

in which
- n may have the values 0 or 1,
- m may have the values 2 or 3,
- and Het represents a heteroaromatic radical of formula

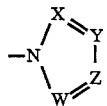

in which

X, Y, Z and W, which may be the same or different, represent a nitrogen atom or a carbon atom linked to a hydrogen atom, a halogen atom, a method radical, an ethyl carboxylate radical, a carboxylic radical or a sulphonic radical, and the pharmaceutically acceptable salts thereof, combined with an ophthalmically acceptable vehicle.

* * * * *

UNITED STATES PATENT AND TRADEMARK OFFICE
CERTIFICATE OF CORRECTION

PATENT NO. : 5,641,781
DATED : June 24, 1997
INVENTOR(S) : Maria Rosa Cuberes-Altisent *et al.*

It is certified that error appears in the above-identified patent and that said Letters Patent is hereby corrected as shown below:

Column 1, line 20, "for" should be --form--.

Column 1, line 22, "meals" should be --mammals--.

Column 1, between lines 25 and 30 --(1)-- should have been printed under first formula.

Column 6, (in Claim 1) between lines 5 and 10 --(1)-- should have been printed under formula Signed and Sealed this Twenty-second Day of June, 1999

Attest:

Q. TODD DICKINSON

*Attesting Officer*   Acting Commissioner of Patents and Trademarks